United States Patent
Fehling et al.

(10) Patent No.: US 6,770,094 B2
(45) Date of Patent: Aug. 3, 2004

(54) INTERVERTEBRAL DISC PROSTHESIS

(76) Inventors: Gerald Fehling, Hanauer Landstr. 7-9, 63791 Karlstein (DE); Guido Fehling, Hanauer Landstr. 7-9, 63791 Karlstein (DE)

( * ) Notice: Subject to any disclaimer, the term of this patent is extended or adjusted under 35 U.S.C. 154(b) by 0 days.

(21) Appl. No.: 10/180,439

(22) Filed: Jun. 26, 2002

(65) Prior Publication Data
US 2003/0009223 A1 Jan. 9, 2003

(30) Foreign Application Priority Data
Jul. 5, 2001 (DE) .......................................... 101 32 588

(51) Int. Cl.⁷ .................................................. A61F 2/44
(52) U.S. Cl. .................................................. 623/17.13
(58) Field of Search ........................... 623/17.11, 17.13, 623/17.15, 17.16

(56) References Cited

U.S. PATENT DOCUMENTS

| | | | | |
|---|---|---|---|---|
| 4,309,777 A | * | 1/1982 | Patil ........................ | 623/17.13 |
| 5,123,926 A | * | 6/1992 | Pisharodi ................. | 623/17.13 |
| 5,458,642 A | * | 10/1995 | Beer et al. ............... | 623/17.13 |
| 5,674,294 A | * | 10/1997 | Bainville et al. ......... | 623/17.16 |
| 5,827,328 A | * | 10/1998 | Buttermann ............. | 623/17.13 |
| 5,989,291 A | * | 11/1999 | Ralph et al. ............. | 623/17.15 |
| 6,019,793 A | * | 2/2000 | Perren et al. ............ | 623/17.16 |
| 6,454,806 B1 | * | 9/2002 | Cohen et al. ............ | 623/17.15 |
| 6,520,996 B1 | * | 2/2003 | Manasas et al. .......... | 623/23.5 |
| 6,582,468 B1 | * | 6/2003 | Gauchet ................... | 623/17.16 |
| 2002/0128714 A1 | * | 9/2002 | Manasas et al. ......... | 623/17.15 |
| 2002/0128715 A1 | * | 9/2002 | Bryan et al. ............. | 623/17.15 |
| 2003/0074076 A1 | * | 4/2003 | Ferree et al. ............ | 623/17.16 |

FOREIGN PATENT DOCUMENTS

| | | |
|---|---|---|
| DE | 198 16 828.4 A1 | 10/1999 |
| EP | 0 706 354 B1 | 2/1999 |
| EP | 0 950 389 A2 | 10/1999 |
| FR | 2 734 148 | 11/1996 |
| WO | WO 95/00082 | 1/1995 |
| WO | WO 95/19153 | 7/1995 |

\* cited by examiner

Primary Examiner—Eduardo C. Robert
(74) Attorney, Agent, or Firm—Pendorf & Cutliff

(57) ABSTRACT

An intervertebral disc prosthesis comprising a cranial disc (10) and a caudal disc (12), which are supported against each other elastically upon compression by spring(s) (16). The spring(s) (16) consist of a memory-metal alloy, which exhibits super-elastic properties at body temperature.

8 Claims, 2 Drawing Sheets

INTERVERTEBRAL DISC PROSTHESIS

BACKGROUND OF THE INVENTION

1. Field of the Invention

The invention concerns an intervertebral disc prosthesis.

2. Description of the Related Art

The intervertebral discs serve as elastic support upon compression between the vertebrae elements of the spinal column. Damage of the intervertebral discs, in particular resulting from degeneration and wear, may lead to severe limitations of mobility and neurological symptoms, in particular pain and paralysis. If such diseases cannot be cured conservatively any more, it is known to fuse the vertebrae elements with each other. Admittedly, this results in the affected vertebrae not being movable relative to each other any longer, so that this leads to a stiffening of the spinal column.

As an alternative, the damaged intervertebral disc may be replaced by an intervertebral disc prosthesis according to the invention. Such intervertebral disc prosthesis consists of an upper cranial disc and a lower caudal disc, between which spring means are inserted, which support these discs elastically upon compression relative to each other. The intervertebral disc prosthesis is inserted between the vertebrae in place of the removed intervertebral disc, whereas the upper and lower discs are anchored to the vertebrae elements of the superior and inferior vertebra. In an intervertebral disc prosthesis, which is known from EP 0 706 354 B1, the spring means are formed by an elastic synthetic cushion. In an intervertebral disc prosthesis, which is known from FR 2 734 148 A1, the spring means are formed by a spring made of titanium or steel, which characteristic response curve causes an exponential increase of the spring tension with decreasing vertebrae distance. These known intervertebral disc prosthesis permit axial and torsion mobility of the vertebrae. Disadvantageously, the material of the spring means is liable to fatigue, which leads to a reduction in of effectiveness of the intervertebral disc prosthesis, and with metal springs, yet may lead to breakage.

SUMMARY OF THE INVENTION

It is the task of the invention to provide an intervertebral disc prosthesis, which combines good mobility of the vertebrae with long-lasting effectiveness.

The substantial idea of the invention is to manufacture the spring means of the intervertebral disc prosthesis using a memory-metal alloy, which comprises super-elastic properties at body temperature. The super-elasticity, which is also named pseudo-elasticity, is based on a tension-induced conversion of austenite to martensite. This reversible conversion of the crystal structure allows a substantially greater elastic deformation in contrast to the Hooke's elasticity of conventional materials and in particular conventional metals, like e.g. steel or titanium. Since the super-elastic deformation is based on a conversion of the crystal structure and not, as with the conventional Hooke'elasticity, on a deformation of the crystal structure, the super-elastic deformation does not lead to fatigue of material. Thus, the elastic properties of the intervertebral disc prosthesis remain unchanged, even after long periods of implantation and a corresponding high number of load alterations, and fatigue break of the spring means need not be feared.

The use of memory-metal alloy for the manufacture of the spring means allows great latitude in the design of the spring means. These may be fine-tuned with respect to their elastic properties and their spring tension. Optimal adjustment of the spring characteristic response curve with respect to both axial movement and torsion movement of the vertebrae is possible.

In one embodiment, the spring means may be in the form of a helical compression spring. Such compression spring allows a particular favorable mobility of the vertebrae with respect to axial movements, tilt movements and torsion movements.

If the spring means is in the form of a disk spring, a good axial and tilt mobility may be realized, together with increased stiffness, where appropriate, whereas no or only slight torsion mobility exists.

In a further embodiment, the spring means may be formed by a spiral spring, which lies between the discs in the form of a toroid or annular spring. Such spiral spring allows axial mobility by means of pressing the spiral spring vertically along its axis. Tilting the coils of the spiral spring towards its axis allows torsion movement. Finally, the spring means may also be formed by one or more flat springs. With such flat springs, particular soft axial shock absorption is obtained. Torsion movements are more or less possible, depending on the width of the flat springs.

The intervertebral disc prosthesis is preferably inserted for that region of the spinal column, which requires a particular high mobility, i.e. in particular for the region of the lumbar vertebrae and the lower thoracic vertebrae. The construction and the dimension of the spring means may therein be chosen according to the application of the intervertebral disc prosthesis, in particular according to the required axial elasticity and the desired torsion mobility.

Preferably, a flexible protective coating covers the spring means formed by the memory-metal alloy in order to prevent tissue from growing into it, which could impair the spring characteristics of the spring means. The protective coating preferably consists of a biocompatible continuously elastic synthetic material.

BRIEF DESCRIPTION OF THE DRAWING

In the following the invention will be described in greater detail on the basis of illustrative embodiments shown in the drawing. There is shown in FIG. 1 in schematic manner a first embodiment of the intervertebral disc prosthesis in axial section, FIG. 2 a corresponding illustration of a second embodiment, FIG. 3 a corresponding illustration of a third embodiment and FIG. 4 a corresponding illustration of a fourth embodiment.

DETAILED DESCRIPTION OF THE INVENTION

The intervertebral disc prosthesis comprises an upper cranial disc 10 and a lower caudal disc 12. The discs 10 and 12 are manufactured of a rigid biocompatible material, preferably titanium. The form of the cross-section of the discs 10 and 12 substantially corresponds to the form of the natural intervertebral disc and the vertebra element, respectively. On the outer surfaces of the discs 10 and 12 spikes 14 are formed, which serve to anchor the discs 10 and 12 to the adjacent faces of the vertebrae elements, while the intervertebral disc prosthesis is inserted between two vertebrae. The discs 10 and 12 are axially spaced and are supported against each other by spring means, which are elastic upon compression.

Figure 1:
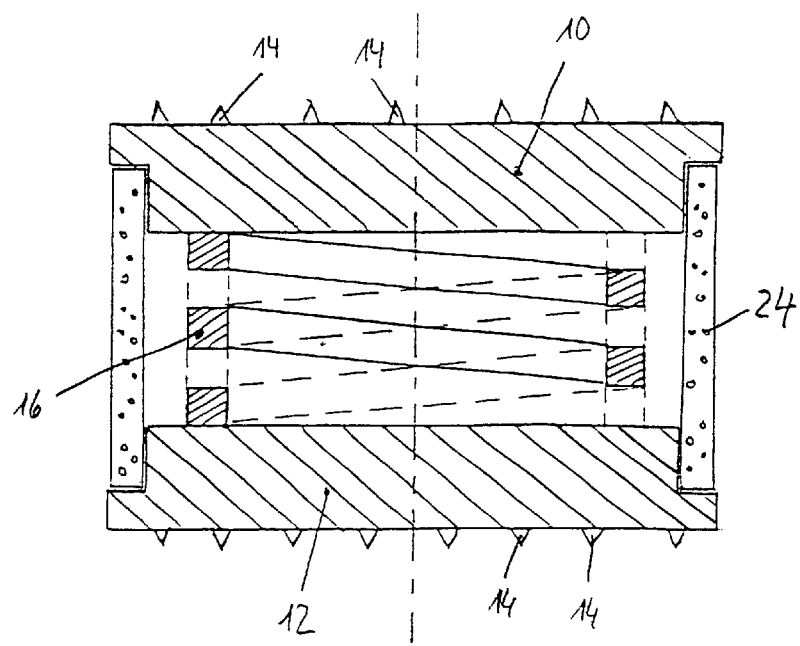
Figure 2:
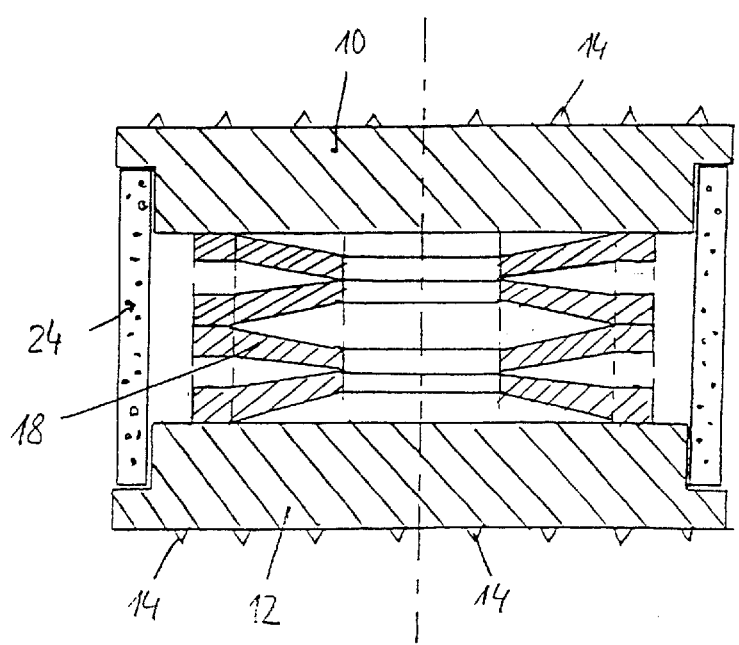

In the embodiment shown in FIG. 1, these spring means are formed by a compression spring 16; in the embodiment shown in FIG. 2, by a stack of disk springs 18. The compression spring 16 and the disk springs 18, respectively, are symmetrically inserted between the discs 10 and 12. Thus, the discs 10 and 12 may, against the pressure of the compression springs 16 and the disk springs 18, respectively, be pressed axially against each other and tilted relative to each other. Additionally, the compression spring 16 of the embodiment in FIG. 1 allows a certain reciprocal torsion of the discs 10 and 12. With the disk springs 18, such torsion is not possible or only possible to a very small extent.

Figure 3:
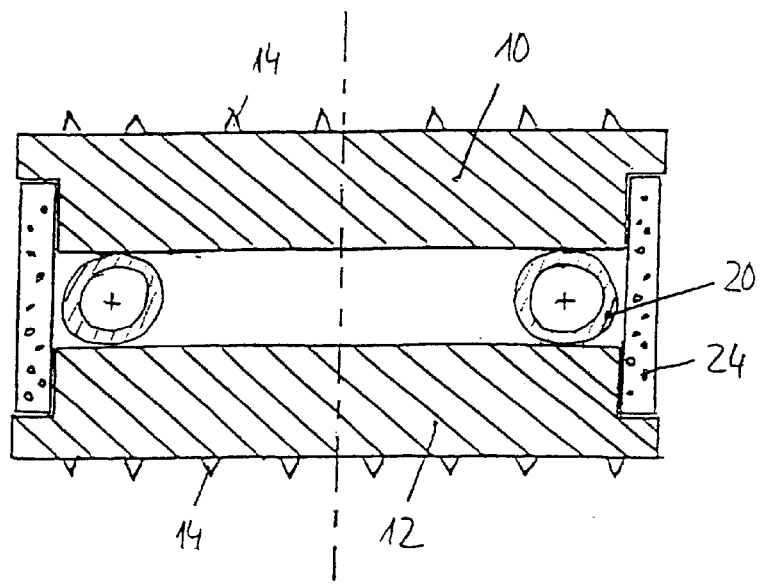

In the embodiment shown in FIG. 3, the spring means are formed by a spiral spring 20, which is set around the circumference of the discs 10 and 12 in the form of a toroid. By means of a deformation of the coils of the spiral spring 20, the discs 10 and 12 may be pressed axially against each other and tilted relative to each other. Torsion movement of the discs 10 and 12 is possible by means of inclining the coils of the spiral spring 20 against their axis.

Figure 4:
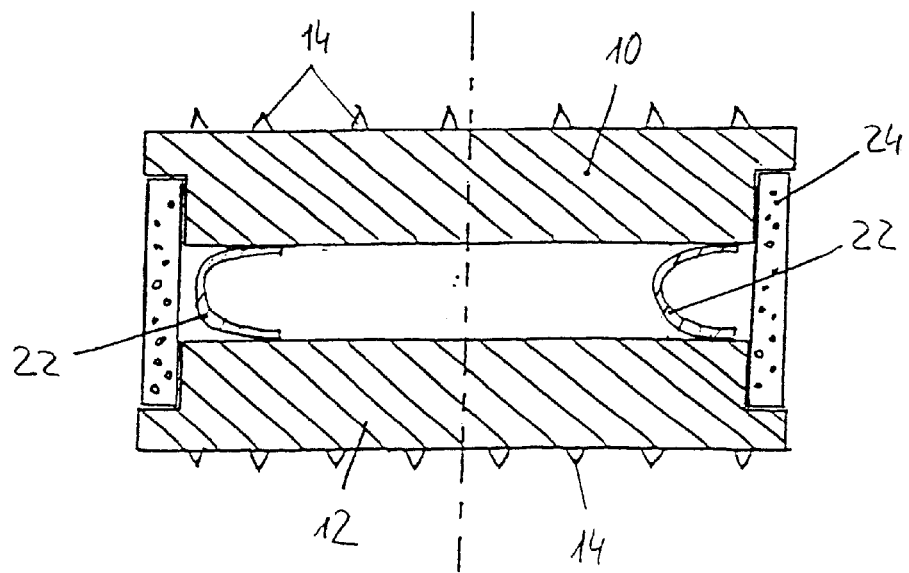

In the embodiment shown in FIG. 4, the spring means are formed by leaf springs 22. These leaf springs 22 have the form of strips, one end of which is mounted on the upper disc 10 and the other end of which is mounted on the lower disc 12. The flat springs 22 are bent U-shaped, whereas they may be vaulted outwardly, as shown in FIG. 4 on the left, or they may be vaulted inwardly, as shown in FIG. 4 on the right. At least three, however preferably six or more of such leaf springs 22 are arranged along the circumference of the discs 10 and 12 with equal angular separation. The leaf springs 22 allow particular soft axial shock absorption, which in particular additionally allows a tilting of the discs 10 and 12. Torsion movement is only possible if the flat springs 22 have a small width (along the circumferential direction of the discs 10 and 12).

Instead of single U-shaped bent leaf springs 22, as depicted in FIG. 4, a single leaf spring may also be provided, which is symmetrically arranged between the disks 10 and 12 and which comprises along its circumference with equal angular separation radially outwardly directed arms, which are alternately mounted to the upper disc 10 and the lower disc 12.

The spring means 16, 18, 20 and 22 are manufactured of a memory-metal alloy, which comprises super-elastic properties in the range of body temperature (35° C. to 40° C.). Such memory-metal alloy may for example be a nickel-titanium-alloy.

In order to prevent tissue from growing into the intervertebral disc prosthesis, a protective coating 24 is provided. The protective coating 24 consists of a biocompatible synthetic material, which is sufficiently soft and continuously elastic in order to avoid interference with the mobility of the intervertebral disc prosthesis.

In the depicted embodiment, the protective coating 24 is in the form of a thin-walled cylindrical sleeve, of which the exposed ends are wound up on the cranial disc 10 and the caudal disc 12, respectively, and which are sealed and mounted appropriately.

What is claimed is:

1. Intervertebral disc prosthesis comprising:

a cranial disc, a caudal disc which is substantially parallel and axially spaced from the cranial disc, and spring means inserted between these discs, which, at body temperature, support these discs elastically upon compression axially against each other, wherein the spring means (16, 18) consist of a memory-metal alloy, which comprises super-elastic properties at body temperature.

2. Intervertebral disc prosthesis according to claim 1, wherein the spring means (16, 18) consist of a super-elastic nickel-titanium-alloy.

3. Intervertebral disc prosthesis according to claim 1, wherein the spring means are formed by a compression spring (16), which is arranged symmetrically between the discs (10, 12).

4. Intervertebral disc prosthesis according to claim 1, wherein the spring means are formed by disk springs (18).

5. Intervertebral disc prosthesis according to claim 1, wherein the spring means are formed by a spiral spring (20), which is arranged between the discs (10, 12) in the form of a toroid.

6. Intervertebral disc prosthesis according to claim 1, wherein the spring means are formed by one or more vaulted leaf springs (22).

7. Intervertebral disc prosthesis according to claim 1, wherein the spring means (16, 18, 20, 22) are enclosed by a protective coating (24).

8. Intervertebral disc prosthesis according to claim 7, wherein the protective coating (24) is a cylindrical sleeve of a soft continuously elastic biocompatible synthetic material.

* * * * *